(12) United States Patent
Liu et al.

(10) Patent No.: US 11,633,242 B2
(45) Date of Patent: Apr. 25, 2023

(54) DEFORMABLE MECHANISM WITH COMBINED MOTION

(71) Applicant: SHENYANG INSTITUTE OF AUTOMATION, CHINESE ACADEMY OF SCIENCES, Liaoning (CN)

(72) Inventors: Hao Liu, Liaoning (CN); Guohao Jiang, Liaoning (CN); Yuanyuan Zhou, Liaoning (CN); Lianqing Liu, Liaoning (CN); Zhongtao Zhang, Liaoning (CN); Wei Guo, Liaoning (CN)

(73) Assignee: SHENYANG INSTITUTE OF AUTOMATION, CHINESE ACADEMY OF SCIENCES, Liaoning (CN)

( * ) Notice: Subject to any disclaimer, the term of this patent is extended or adjusted under 35 U.S.C. 154(b) by 430 days.

(21) Appl. No.: 16/762,488

(22) PCT Filed: Jan. 16, 2019

(86) PCT No.: PCT/CN2019/071870
§ 371 (c)(1),
(2) Date: May 7, 2020

(87) PCT Pub. No.: WO2020/118848
PCT Pub. Date: Jun. 18, 2020

(65) Prior Publication Data
US 2021/0177529 A1 Jun. 17, 2021

(30) Foreign Application Priority Data
Dec. 13, 2018 (CN) .......................... 201811523334.1

(51) Int. Cl.
  *A61B 34/30* (2016.01)
  *A61B 34/00* (2016.01)
  *A61B 17/00* (2006.01)

(52) U.S. Cl.
  CPC .............. *A61B 34/30* (2016.02); *A61B 34/71* (2016.02); *A61B 34/77* (2016.02);
  (Continued)

(58) Field of Classification Search
  None
  See application file for complete search history.

(56) References Cited

U.S. PATENT DOCUMENTS

| 2008/0065099 | A1* | 3/2008 | Cooper | ............ A61B 17/00234 901/14 |
| 2015/0080908 | A1* | 3/2015 | Lathrop | ................. A61B 17/29 606/130 |
| 2016/0206388 | A1 | 7/2016 | Prisco | |

FOREIGN PATENT DOCUMENTS

| CN | 1870930 A | 11/2006 |
| CN | 104799890 A | 7/2015 |

(Continued)

*Primary Examiner* — Kawing Chan
(74) *Attorney, Agent, or Firm* — Novick, Kim & Lee, PLLC; Allen Xue

(57) ABSTRACT

A deformable segment with combined motion includes a flexible center backbone, the tendons of deformable segment with combined motion, a connecting piece, a proximal disk and a distal disk. The proximal end of the flexible center backbone and the proximal ends of the tendons of deformable segment with combined motion are fixedly connected to the proximal disk. The distal ends of the tendons of deformable segment with combined motion are fixedly connected to the distal disk. The distal end of the flexible center backbone penetrates through the distal disk and then extends into the distal execution segment, and is connected with the end-effector. The deformable segment with combined motion is (Continued)

provided with the connecting piece. The proximal driving segment is provided with proximal driving tendons. The proximal driving tendons penetrate through the proximal disk, and then are fixedly connected with the connecting piece.

9 Claims, 10 Drawing Sheets

(52) U.S. Cl.
CPC ............... *A61B 2017/00323* (2013.01); *A61B 2034/301* (2016.02); *A61B 2034/306* (2016.02)

(56) References Cited

FOREIGN PATENT DOCUMENTS

| | | |
|---|---|---|
| CN | 106163421 A | 11/2016 |
| CN | 108030518 A | 5/2018 |
| CN | 108354667 A | 8/2018 |

* cited by examiner

DEFORMABLE MECHANISM WITH COMBINED MOTION

TECHNICAL FIELD

The present invention relates to the technical field of medical instruments, and more particularly relates to a deformable mechanism with combined motion.

BACKGROUND

With the development of science and technology, the robot technology is more and more widely used. The application of the robot technology to medical surgery can greatly improve the operation accuracy and quality of surgeries, ensure safe and smooth execution of the surgeries, improve the surgical environment of doctors and shorten the recovery time of patients. When the robot technology is applied to the medical field, if the robot technology can be combined with a dexterous minimally invasive surgical instrument that can be deformed in a certain space range, not only the operating range of the minimally invasive surgical instrument can be expanded to reach a place that cannot be reached by a conventional instrument in a limited surgical hole, but also anatomical dispositions can be adapted. However, in order to achieve the above purpose, it is necessary to ensure that the minimally invasive surgical instrument meets the requirements of deformation capability, small size, high load capacity and the like, and also to ensure the control precision. It is difficult for the mechanism in the prior art to meet the above requirements.

SUMMARY

The purpose of the present invention is to provide a deformable mechanism with combined motion. A deformable segment with combined motion is used to deform to realize the expansion space required for surgeries such as single port laparoscopic surgery without influencing the actions of a distal execute segment and an end-effector. The distal execute segment and the end-effector still have high flexibility and can better assist the doctors in completing the surgeries. The integral structure is compact and meets the requirements of deformation capability, small size, high load capacity and the like for the instrument.

The purpose of the present invention is realized by the following technical solution:

A deformable mechanism with combined motion comprises a proximal driving segment, a deformable segment with combined motion, a distal execution segment and an end-effector, wherein the deformable segment with combined motion comprises a flexible center backbone, the tendons of deformable segment with combined motion, a connecting piece, a proximal disk and a distal disk; the proximal end of the flexible center backbone and the proximal end of the tendons of deformable segment with combined motion are fixedly connected to the proximal disk; the distal end of the tendons of deformable segment with combined motion are fixedly connected to the distal disk; the distal end of the flexible center backbone penetrates through the distal disk and then extends into the distal execution segment, and is connected with a connecting disk at the end-effector; the deformable segment with combined motion is provided with the connecting piece; the proximal driving segment is provided with a plurality of proximal driving tendons; the proximal driving tendons penetrate through the proximal disk of the deformable segment with combined motion, and then are fixedly connected with the connecting piece; the distal execution segment comprises a plurality of distal driving tendons; the distal ends of the distal driving tendons are fixedly connected to the connecting disk at the end-effector; and the proximal ends of the distal driving tendons penetrate through the deformable segment with combined motion and the proximal driving segment and then extend out.

The deformable segment with combined motion is provided with a deformation segment transition disk; the distal execution segment is provided with an execution segment transition disk; and the deformation segment transition disk and the execution segment transition disk are provided with a plurality of through holes.

The deformable segment with combined motion is provided with a tightly wound spring; and the distal driving tendons extend along the tightly wound spring after stretching into the corresponding tightly wound spring.

An inner passage is arranged in each tendon of deformable segment with combined motion; and the distal driving tendons extend along the inner passage in the corresponding the tendons of deformable segment with combined motion.

The flexible center backbone is provided with spring layers of different rotating directions, and the interior of the flexible center backbone is hollow.

The deformable segment with combined motion and the proximal driving segment are connected through the connecting piece; and outer skeletons are sleeved outside the proximal driving segment, the deformable segment with combined motion and the distal execution segment.

The outer skeletons are transition disks, slot type outer skeletons, disk type outer skeletons, spring outer skeletons, disc spring skeletons or bellows outer skeletons.

A plurality of passages are arranged in the outer skeletons.

The end-effector comprises a rotating seat, a connecting disk, an opening and closing push-pull rod, an opening and closing driving tendon and a torque sheath pipe; the rotating seat is rotatably arranged on the connecting disk; a movable opening and closing push-pull rod is arranged in the rotating seat; the connecting disk is connected with the flexible center backbone; a torque sheath pipe for driving rotation of the rotating seat is arranged in the flexible center backbone; and the opening and closing driving tendon for driving the opening and closing push-pull rod to move is arranged in the torque sheath pipe.

A chute is arranged in the rotating seat; a slide block is arranged in the chute; a spring is arranged between the slide block and the bottom of the chute; the rear end of the opening and closing push-pull rod is abutted against the slide block; and the opening and closing driving tendon penetrates through the slide block and the spring and then is fixedly connected with the opening and closing push-pull rod.

The present invention has the advantages and positive effects that:

1. The present invention uses the deformable segment with combined motion to deform to realize the expansion space required for surgeries such as single port laparoscopic surgery without influencing the actions of a distal execute segment and an end-effector. The distal execute segment and the end-effector still have high flexibility and can better assist the doctors in completing the surgeries.

2. The integral structure of the present invention is compact, can realize complicated morphologic change of the deformable segment with combined motion, has torsion resistant characteristic, can ensure deformation rigidity, reduces movement coupling and can meet the requirements of deformation capability, small size, high load capacity and the like for the instrument.

3. The linkage design of the present invention realizes the expansion of the single-hole surgical instrument in two degrees of freedom during the surgery, and reduces the number of surgical instrument driving tendons. The inner flexible center backbone can deform in two degrees of freedom, and has axial incompressibility characteristic and good torsion resistant characteristic around the axis direction. In addition, outer skeletons of different structural forms can be sleeved on the deformable segment with combined motion, so that the use is flexible and convenient.

In the figures, 1 proximal driving segment; 101 proximal driving tendon; 102 outer cover; 2 deformable segment with combined motion; 201 flexible center backbone; 2011 right-handed spring; 2012 left-handed spring; 2013 end ring; 202 the tendons of deformable segment with combined motion; 203 connecting piece; 204 deformation segment transition disk; 2041 center shaft through hole; 2042 tendon through hole; 2043 transition through hole; 205 proximal disk; 206 distal disk; 207 reinforcing tendon; 208 tightly wound spring; 209 driving deformation part; 210 linkage deformation part; 3 distal execution segment; 301 execution segment transition disk; 302 distal driving tendon; 4 end-effector; 401 connecting disk; 402 opening and closing driving tendon; 403 torque sheath pipe; 404 rotating seat; 405 opening and closing push-pull rod; 406 connecting rod assembly; 407 spring; 408 slide block; 5 slot type outer skeleton; 501 skeleton outer wall; 502 first tendon passage; 503 inner plate; 504 first tightly wound spring passage; 505 cutting groove; 506 first middle passage; 6 disk type outer skeleton; 601 first middle through hole; 602 first tightly wound spring hole; 603 first tendon through hole; 604 disk surface; 7 spring outer skeleton; 701 second center shaft passage; 702 second tightly wound spring passage; 703 second tendon passage; 8 disc spring backbone; 801 second middle through hole; 802 second tightly wound spring hole; 803 second tendon through hole; 804 disc cone end; 805 wave trough; 806 wave peak; 9 bellows; 901 skeleton passage; and 902 passage.

DETAILED DESCRIPTION

The present invention is further detailed below in combination with the drawings.

Figure 1:
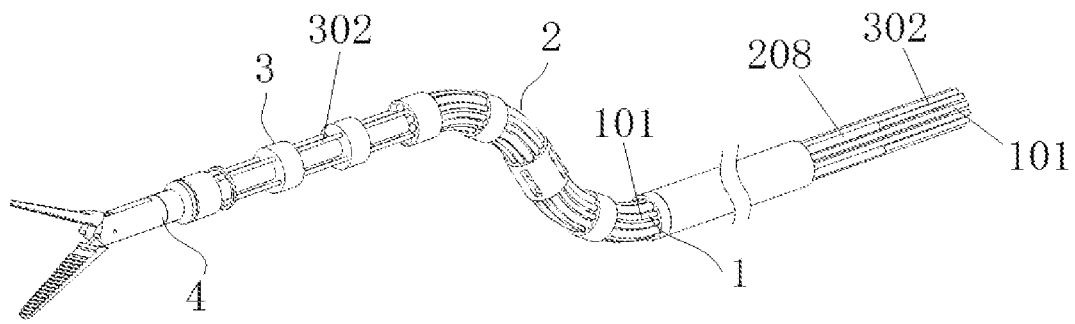
FIG. 1 is a structural schematic diagram of the present invention.
Figure 2:
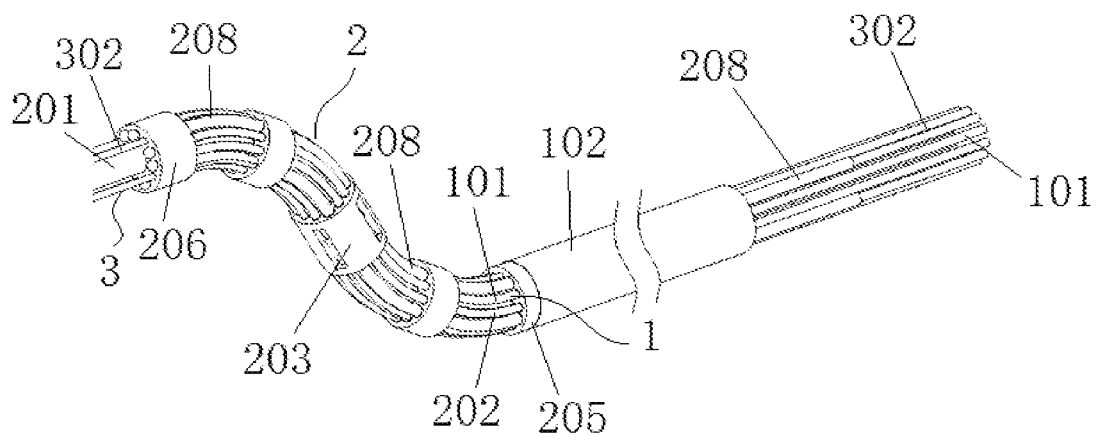
FIG. 2 is a partial enlarged drawing of the present invention in FIG. 1.
Figure 4:
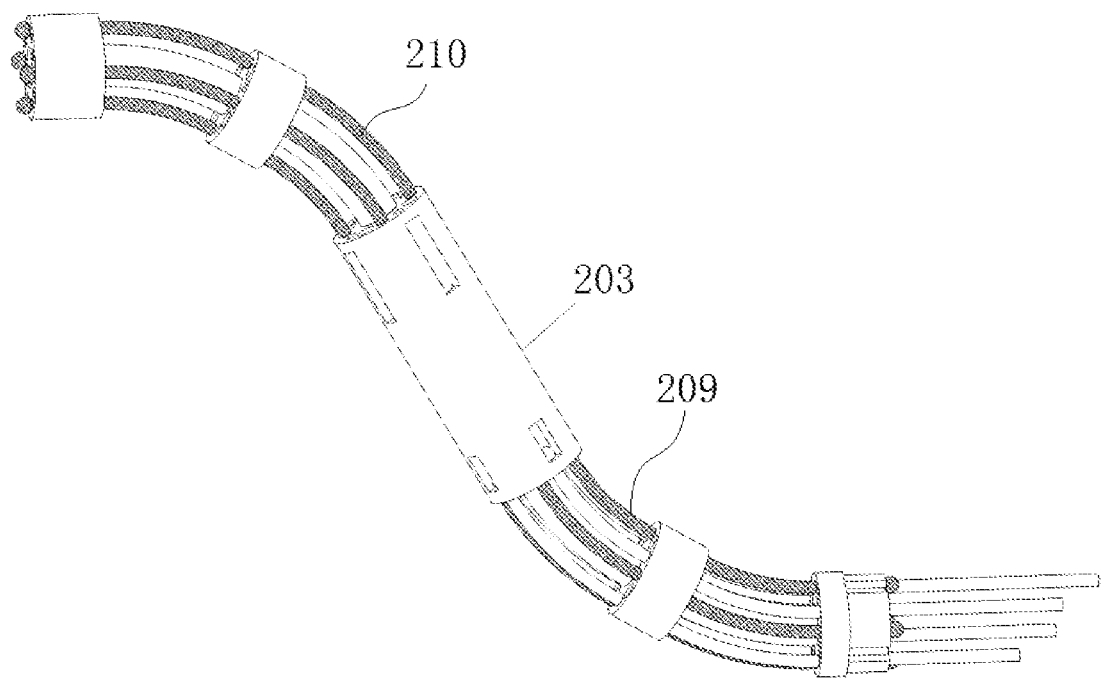
FIG. 4 is a schematic diagram of a deformable segment with combined motion which adopts a lengthened connecting piece in FIG. 3.
Figure 5:
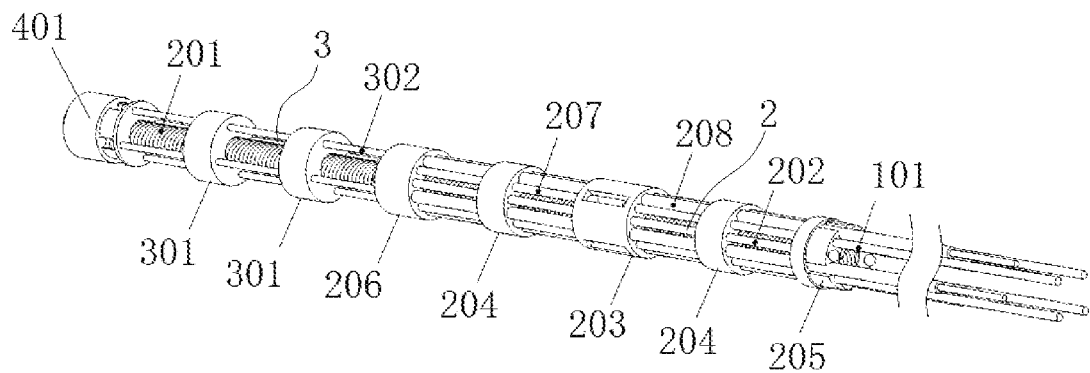
FIG. 5 is a schematic diagram when the present invention is straightened in FIG. 2.

As shown in FIGS. 1-21, the present invention comprises a proximal driving segment 1, a deformable segment with combined motion 2 and a distal execution segment 3, wherein the deformable segment with combined motion 2 comprises a flexible center backbone 201, the tendons of deformable segment with combined motion 202, a connecting piece 203, a proximal disk 205 and a distal disk 206; a plurality of the tendons of deformable segment with combined motion 202 are evenly distributed on the outer side of the flexible center backbone 201; the proximal end of the flexible center backbone 201 and the proximal ends of the tendons of deformable segment with combined motion 202 are fixedly connected to the proximal disk 205; the distal ends of the tendons of deformable segment with combined motion 202 are fixedly connected to the distal disk 206; as shown in FIGS. 2 and 5, the distal end of the flexible center backbone 201 penetrates through the distal disk 206 and then extends into the distal execution segment 3, and is connected with a connecting disk 401 at the end-effector 4; the middle of the deformable segment with combined motion 2 is provided with the connecting piece 203; the flexible center backbone 201 and the tendons of deformable segment with combined motion 202 penetrate through the connecting piece 203; as shown in FIGS. 2 and 5-7, the proximal driving segment 1 is provided with a plurality of proximal driving tendons 101; the proximal driving tendons 101 penetrate through the proximal disk 205 of the deformable segment with combined motion 2, and then are fixedly connected with the proximal end of the connecting piece 203; the distal execution segment 3 comprises a plurality of distal driving tendons 302; the distal ends of the distal driving tendons 302 are fixedly connected to the connecting disk 401 at the end-effector 4; and the proximal ends of the distal driving tendons 302 penetrate through the deformable segment with combined motion 2 and the proximal driving segment 1 and then extend out for control. The proximal driving tendons 101, the distal driving tendons 302 and the tendons of deformable segment with combined motion 202 are evenly distributed around the flexible center backbone 201.

Figure 3:
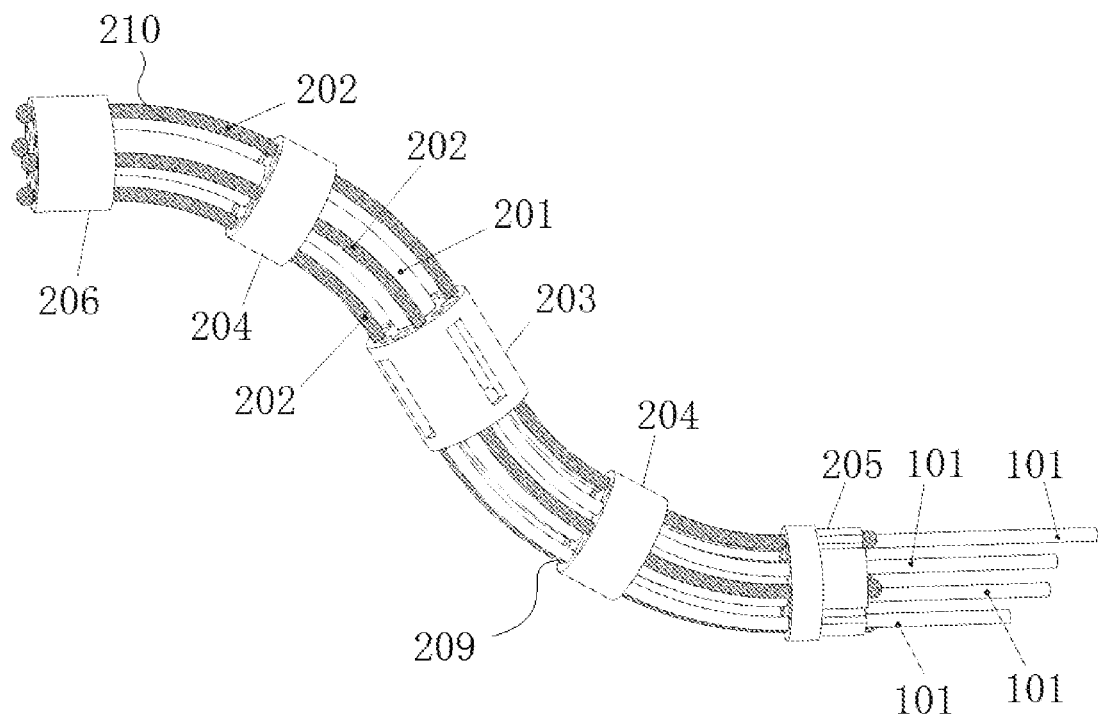
FIG. 3 is a structural schematic diagram of a deformable segment with combined motion in FIG. 2.

When the mechanism works, the mechanism pulls the proximal driving tendon 101 to move to realize the deformation of the proximal driving segment 1, and pulls the distal driving tendon 302 to move to realize the deformation of the distal execution segment 3. As shown in FIGS. 3-4, the motion of the proximal driving tendon 101 can be transmitted to the connecting piece 203 in the middle of the deformable segment with combined motion 2 so as to deform the deformable segment with combined motion 2 to realize the expansion space required for surgeries such as single port laparoscopic surgery. Moreover, each proximal driving tendon 101 is pulled to move to realize deformation of the deformable segment with combined motion 2 in one direction. The purpose of changing the quantity of freedoms required by the deformable segment with combined motion 2 can be achieved by controlling the quantity of the proximal driving tendons 101. In addition, because the sum of lengths of the deformable segment with combined motion 2 remains unchanged during the linkage expansion deformation, the length of the distal driving tendon 302 in the deformable segment with combined motion 2 is not changed. Therefore, the deformation of the deformable segment with combined motion 2 does not affect the deformation of the distal execution segment 3 and the end-effector 4.

As shown in FIGS. 2-4, the deformable segment with combined motion 2 is divided into two parts: a driving deformation part 209 and a linkage deformation part 210 by the connecting piece 203. The distal execution segment 3 is connected with the linkage deformation part 210. The proximal driving segment 1 is connected with the driving deformation part 209. The proximal driving tendon 101 in the proximal driving segment 1 is fixedly connected with the connecting piece 203 after penetrating through the driving deformation part 209, to drive the deformation of the deformable segment with combined motion 2. The length of the driving deformation part 209 and the length of the linkage deformation part 210 may be the same, and the tendons of deformable segment with combined motion 202 adopts the same arrangement radius. When the expansion motion of the linkage instrument is realized, the attitude of the distal disk 206 of the deformable segment with combined motion 2 remains unchanged. In addition, the connecting piece 203 can also realize the deformation angle adjustment by transitioning the tendons of deformable segment with combined motion 202 with different arrangement radius. For the tendons of deformable segment with combined motion 202, when the arrangement radius of the driving deformation part 209 is greater than the arrangement radius of the linkage deformation part 210 (that is, when the length of the driving deformation part 209 is greater than that of the linkage deformation part 210), the deformation angle of the linkage deformation part 210 is greater than the deformation angle of the driving deformation part 209. Conversely, the deformation angle of the linkage deformation part 210 is smaller than the deformation angle of the driving deformation part 209. Or, as shown in FIGS. 3-4, the deformable segment with combined motion 2 can also adjust the expansion space by changing the length of the connecting piece 203.

Figure 6:
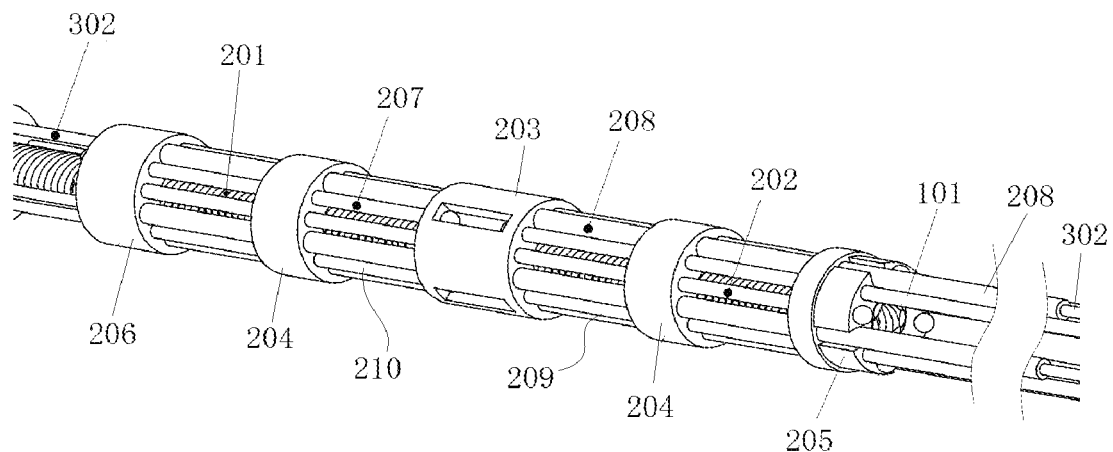
FIG. 6 is a partial enlarged drawing of FIG. 5.
Figure 7:
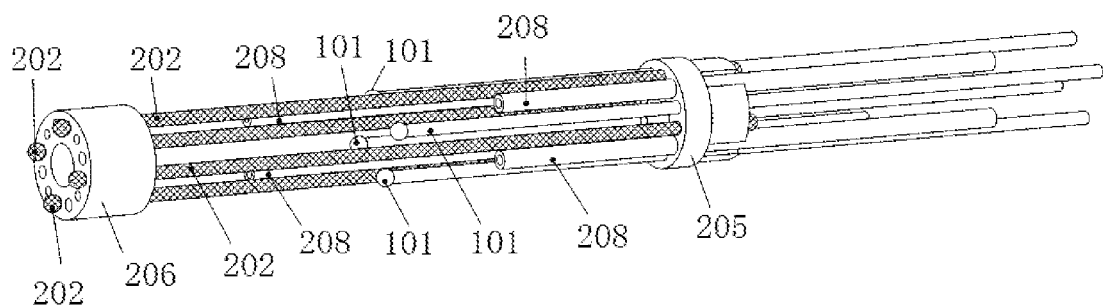
FIG. 7 is a schematic diagram of arrangement of each tendon of a deformable segment with combined motion in FIG. 5.
Figure 20:
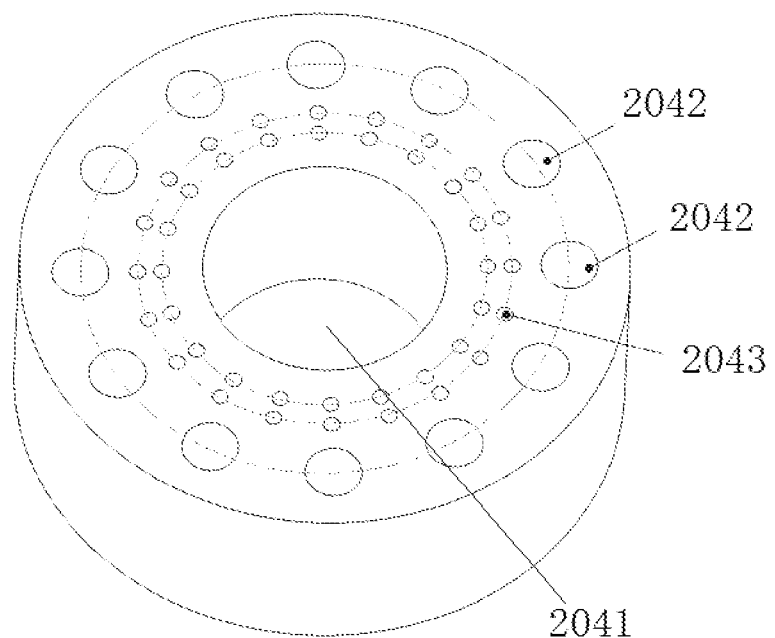
FIG. 20 is a structural schematic diagram of a transition disk in FIG. 3.

As shown in FIG. 3 and FIGS. 5-6, the driving deformation part 209 and the linkage deformation part 210 are provided with deformation segment transition disks 204 for restricting each tendon from dispersing, so as to ensure a linkage deformation action. As shown in FIG. 20, center shaft through holes 2041 for the flexible center backbone 201 to penetrate through, tendon through holes 2042 for each tendon to pass through, and transition through holes 2043 for other elements to penetrate through are arranged in the middles of the deformation segment transition disks 204. In addition, as shown in FIG. 5, the distal execution segment 3 is provided with a plurality of execution segment transition disks 301 for restricting each tendon from dispersing, so as to ensure the linkage deformation action. The structures of the execution segment transition disks 301 are the same as the structures of the deformation segment transition disks 204, and are also provided with a plurality of through holes for different elements to penetrate through. In addition, as shown in FIG. 6, a reinforcing tendon 207 is also arranged on the linkage deformation part 210 in addition to the tendons of deformable segment with combined motion 202, to further ensure the deformation action.

As shown in FIGS. 1-2 and FIGS. 5-7, the driving deformation part 209 and the linkage deformation part 210 of the deformable segment with combined motion 2 are provided with tightly wound springs 208; and the tightly wound springs 208 are evenly distributed around the flexible center backbone 201. The distal driving tendons 302 of the distal execution segment 3 correspond to the tightly wound springs 208 one by one, and the distal driving tendons 302 extend along the tightly wound springs 208 after stretching into the corresponding tightly wound springs 208, and extend out from the proximal end of the proximal driving segment 1. In the present invention, an inner passage is arranged in each tendon of deformable segment with combined motion 202; and the distal driving tendons 302 extend along the inner passage in the corresponding the tendons of deformable segment with combined motion 202.

The tendons of deformable segment with combined motion 202, the proximal driving tendon 101, the distal driving tendons 302, the reinforcing tendon 207, the distal disk 206, the proximal disk 205 and the connecting piece 203 are made of elastic metal (such as spring steel); the end part of each tendon is fixedly connected with the distal disk 206, the proximal disk 205 or the connecting piece 203 in a welding fixation manner; and the above components are also made of polymers.

Figure 8:
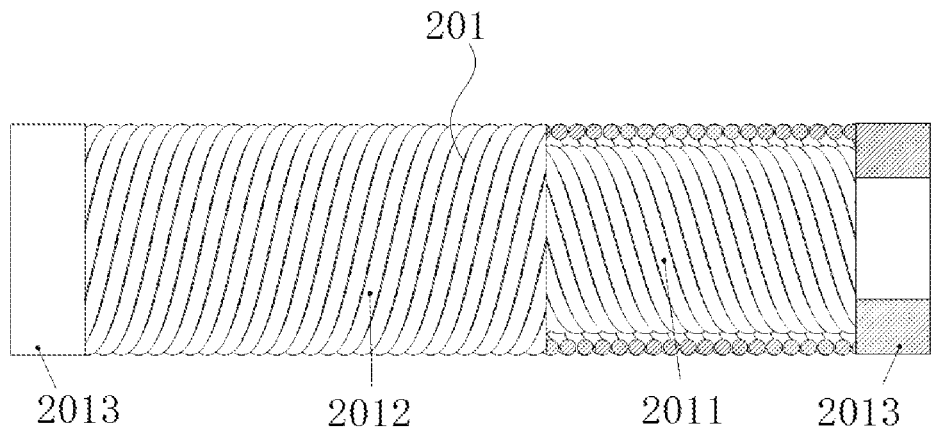
FIG. 8 is a structural schematic diagram of a flexible center backbone in FIG. 2.
Figure 21:
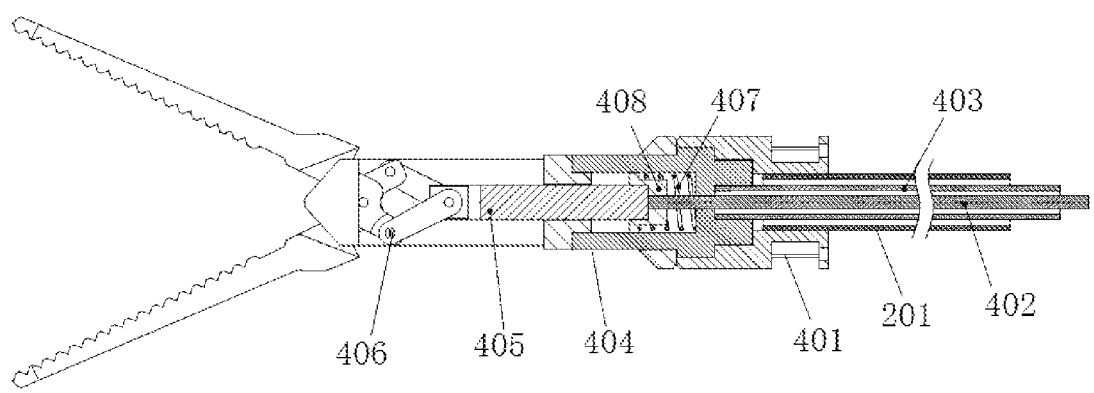
FIG. 21 is a schematic diagram of an end-effector in FIG. 1.

The flexible center backbone 201 is made of multi-strand multi-layer springs of different rotation directions. As shown in FIG. 8, the flexible center backbone 201 comprises a right-handed spring 2011 and a left-handed spring 2012 which are sleeved together, and the end parts of the springs of all layers are fixedly connected by end rings 2013. In this way, the flexible center backbone 201 has the characteristics of axial incompressibility and torsional resistance in two directions around the axis. The arc length of the axis is ensured to be unchanged when the springs deform. As shown in FIG. 21, the interior of the flexible center backbone 201 is hollow; the end-effector 4 is provided with an opening and closing driving tendon 402 and a torque sheath pipe 403; and the opening and closing driving tendon 402 and the torque sheath pipe 403 penetrate through the flexible center backbone 201 and then are connected with respective driving devices. Because the length of the deformable segment with combined motion 2 remains unchanged during the linkage expansion deformation, the lengths of the opening and closing driving tendon 402 and the torque sheath pipe 403 in the deformable segment with combined motion 2 are not changed. Namely, the deformation motion of the deformable segment with combined motion 2 does not affect the action of the end-effector 4.

As shown in FIGS. 9-19, in the present invention, outer skeletons of different forms can be sleeved outside the driving deformation part 209 and the linkage deformation part 210 of the deformable segment with combined motion 2 and the distal execution segment 3, to play a protection role and ensure the deformation action.

The outer skeletons can be composed of a plurality of transition disks. The structures of the transition disks are the same as the structures of the deformation segment transition disk 204 and the execution segment transition disk 301.

Figure 9:
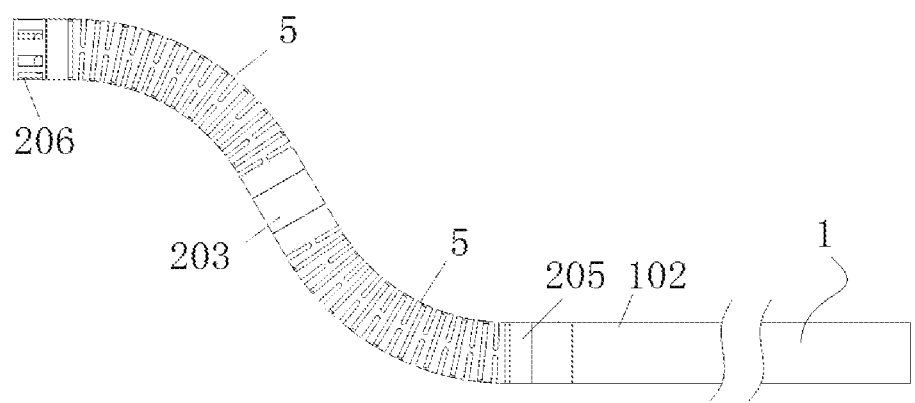
FIG. 9 is a schematic diagram when a deformable segment with combined motion of the present invention is provided with a slot type outer skeleton.
Figure 10:
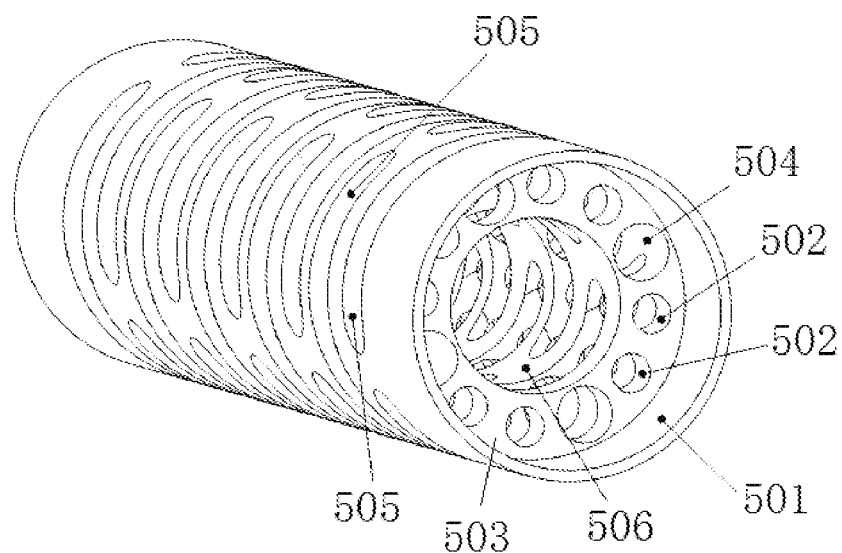
FIG. 10 is a schematic diagram of a slot type outer skeleton in FIG. 8.
Figure 11:
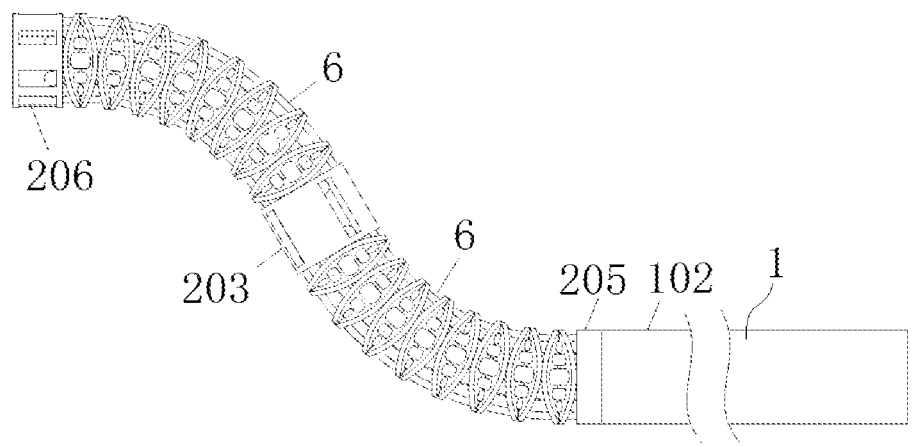
FIG. 11 is a schematic diagram when a deformable segment with combined motion of the present invention is provided with a disk type outer skeleton.
Figure 12:
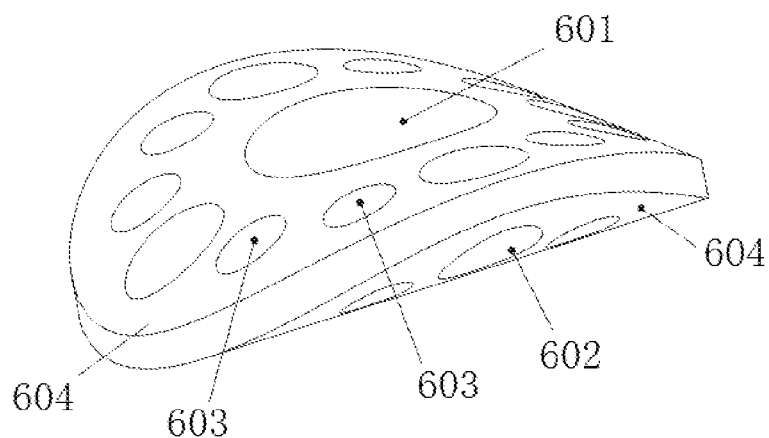
FIG. 12 is a schematic diagram of a crossed disk adopted in a disk type outer skeleton in FIG. 11.
Figure 13:
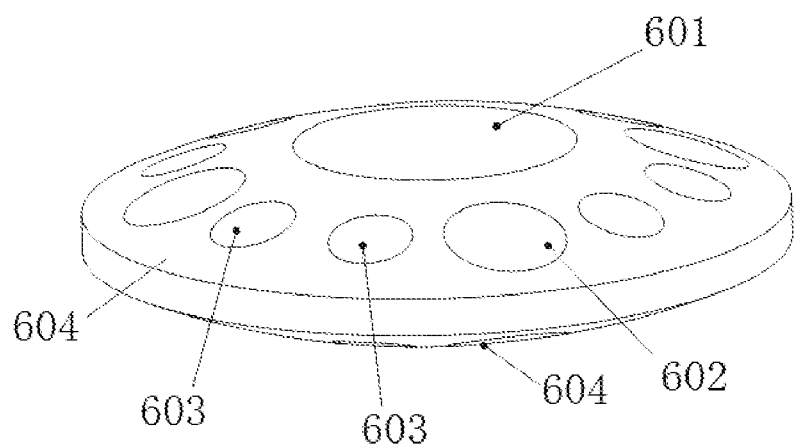
FIG. 13 is a schematic diagram of a dual-sphere disk adopted in a disk type outer skeleton in FIG. 11.
Figure 14:
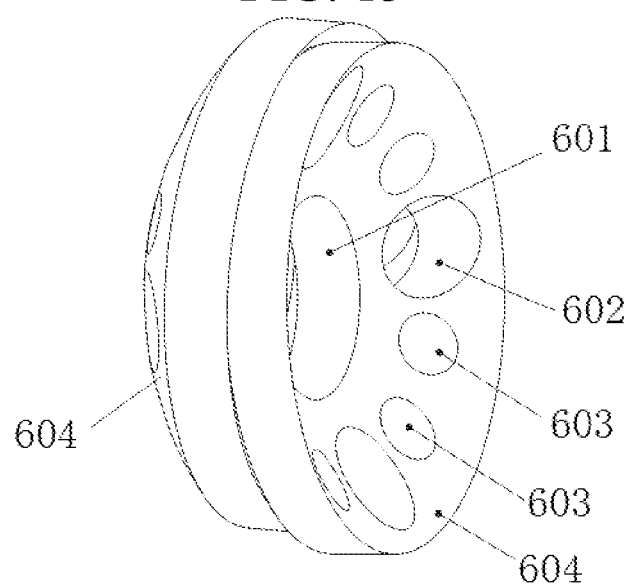
FIG. 14 is a schematic diagram of a ball hinge disk adopted in a disk type outer skeleton in FIG. 11.

As shown in FIGS. 9-10, slot type outer skeletons 5 can be sleeved outside the driving deformation part 209 and the linkage deformation part 210 of the deformable segment with combined motion 2 in the present invention. Each of the slot type outer skeletons 5 comprises a cylindrical skeleton outer wall 501 and a plurality of inner plates 503 arranged in the skeleton outer wall 501. The skeleton outer wall 501 is crisscross provided with a cutting groove 505 to realize flexibility. The plurality of inner plates 503 are provided with through holes, and the through holes of the inner plates 503 respectively correspond to each other to form a first middle passage 506 for the flexible center backbone 201 to pass through, a first tendon passage 502 for the tendons to pass through, and a first tightly wound spring passage 504 for the tightly wound springs 208 to pass through. The slot type outer skeletons 5 can be made of elastic metal (such as spring steel) or polymers. The end parts of the slot type outer skeletons 5 are connected with the distal disk 206, the proximal disk 205 or the connecting piece 203 by bonding or mechanical embedding interference.

As shown in FIGS. 11-14, disk type outer skeletons 6 can be sleeved outside the driving deformation part 209 and the linkage deformation part 210 of the deformable segment with combined motion 2 in the present invention. Each of the disk type outer skeletons 6 comprises a plurality of single disks, and the single disks are crisscross superposed and arranged in a straight line. Each single disk is provided with a first middle through hole 601 for the flexible center backbone 201 to pass through, a first tendon through hole 603 for the tendons to pass through, and a first tightly wound spring hole 602 for the tightly wound springs 208 to pass through. The first middle through holes 601 on the single disks correspondingly form a passage for the flexible center backbone 201 to pass through; the first tendon through holes 603 on the single disks correspondingly form a passage for the tendons to pass through; and the first tightly wound spring holes 602 on the single disks correspondingly form a passage for the tightly wound springs 208 to pass through. The single disks can adopt crossed disks shown in FIG. 12. The upper and lower side disk surfaces 604 of the crossed disks are cylindrical surfaces. The single disks can also adopt dual-sphere disks shown in FIG. 13. The upper and lower side disk surfaces 604 of the dual-sphere disks are spherical surfaces. The single disks can also adopt ball hinge disks shown in FIG. 14. One side disk surface 604 of the ball hinge disks is a concave spherical surface, and the other side disk surface 604 is a convex spherical surface. The convex spherical surface of any ball hinge disk is embedded with the concave spherical surface of the adjacent ball hinge disk on one side. The single disks can be made of elastic metal (such as spring steel) or polymers. The single disks on the end parts of the disk type outer skeletons 6 are directly abutted against the distal disk 206, the proximal disk 205 or the connecting piece 203.

Figure 15:
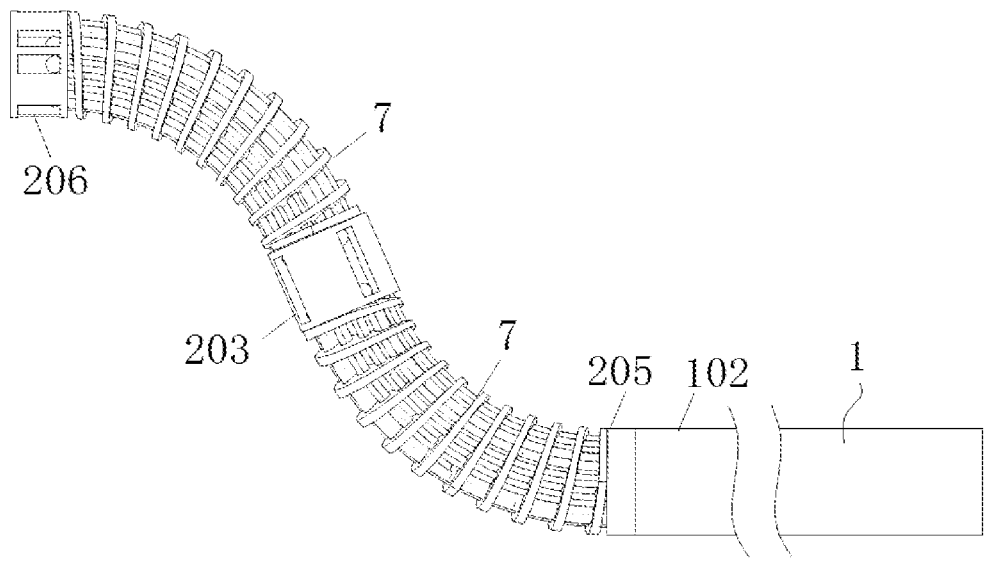
FIG. 15 is a schematic diagram when a deformable segment with combined motion of the present invention is provided with a spring outer skeleton.
Figure 16:
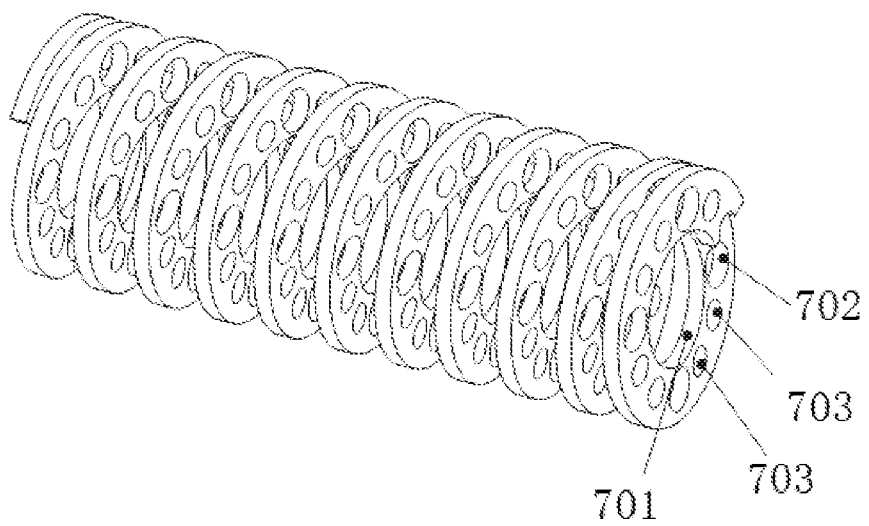
FIG. 16 is a schematic diagram of a spring outer skeleton in FIG. 15.

As shown in FIGS. 15-16, spring outer skeletons 7 can be sleeved outside the driving deformation part 209 and the linkage deformation part 210 of the deformable segment with combined motion 2 in the present invention. Each of the spring outer skeletons 7 is provided with a second center shaft passage 701 for the flexible center backbone 201 to pass through, a second tendon passage 703 for the tendons to pass through, and a first tightly wound spring passage 702 for the tightly wound springs 208 to pass through. The spring outer skeletons 7 can be made of elastic metal (such as spring steel) or polymers. The end parts of the spring outer skeletons 7 are directly abutted against the distal disk 206, the proximal disk 205 or the connecting piece 203.

Figure 17:
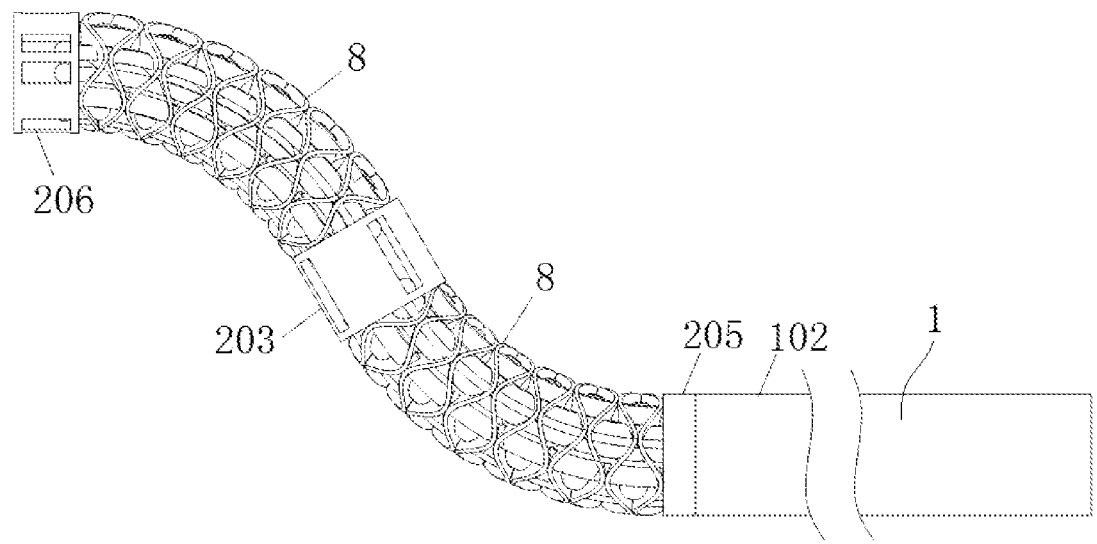
FIG. 17 is a schematic diagram when a deformable segment with combined motion of the present invention is provided with a disc spring skeleton.
Figure 18:
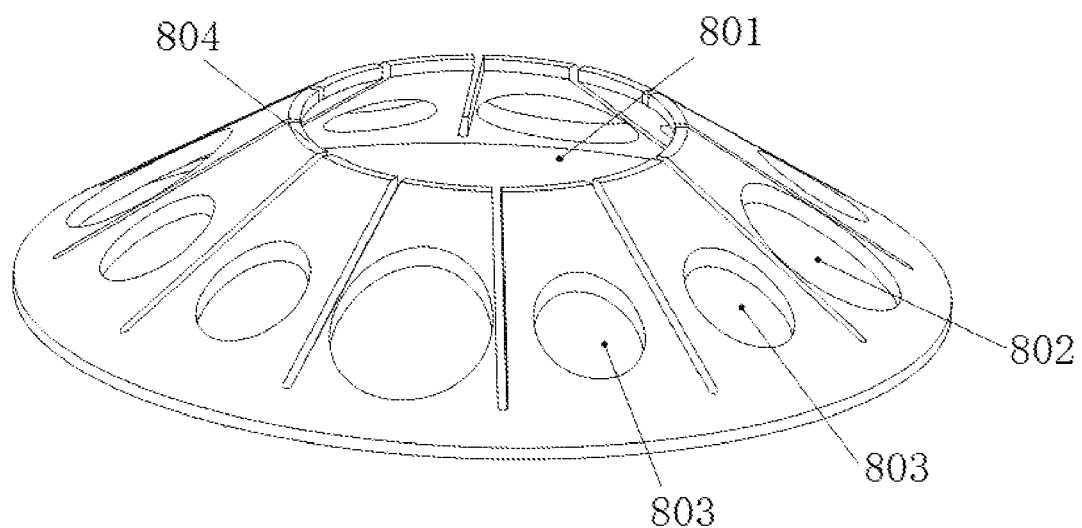
FIG. 18 is a schematic diagram of a conical disc spring adopted in an outer skeleton in FIG. 17.
Figure 19:
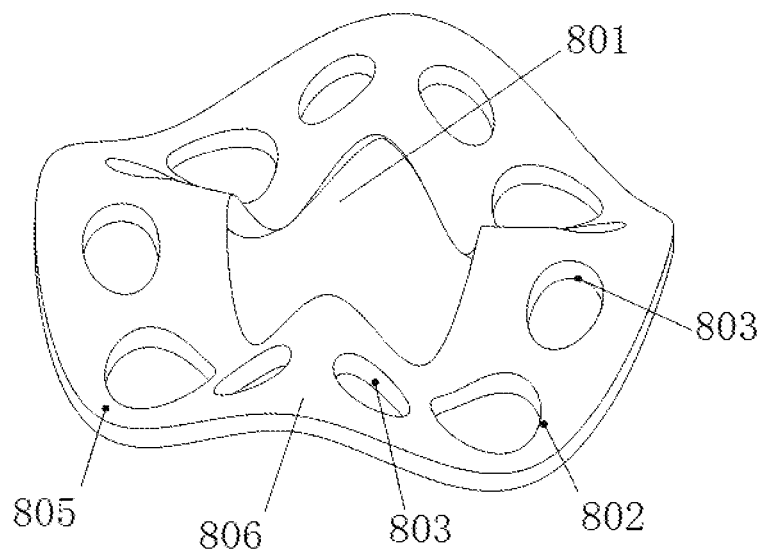
FIG. 19 is a schematic diagram of a wave spring piece adopted in a disc spring skeleton in FIG. 17.

As shown in FIGS. 17-19, disc spring skeletons 8 can be sleeved outside the driving deformation part 209 and the linkage deformation part 210 of the deformable segment with combined motion 2 in the present invention. Each of the disc spring skeletons 8 comprises a plurality of spring pieces, and the single disks are crisscross superposed and arranged in a straight line. Each spring piece is provided with a second middle through hole 801 for the flexible center backbone 201 to pass through, a second tendon through hole 803 for the tendons to pass through, and a second tightly wound spring hole 802 for the tightly wound springs 208 to pass through. The second middle through holes 801 on the spring pieces correspondingly form a passage for the flexible center backbone 201 to pass through; the second tendon through holes 803 on the spring pieces correspondingly form a passage for the tendons to pass through; and the second tightly wound spring holes 802 on the spring pieces correspondingly form a passage for the tightly wound springs 208 to pass through. The spring piece can adopt a conical disc spring shown in FIG. 18, and a disc cone end 804 of any conical disc spring is abutted against the cone end of the adjacent one at one side. The flaring edge of the conical disc spring is abutted against the flaring edge of the adjacent one at the other side. The spring piece can also adopt a wave spring piece shown in FIG. 19. The wave spring piece is crisscross provided with a wave peak 806 and a wave valley 805 along the circumferential direction, and the wave peak 806 of any wave spring piece is abutted against the wave peak 806 of the adjacent wave spring piece on one side. The wave valley 805 of the wave spring piece is abutted against the wave valley 805 of the adjacent wave spring piece on the other side. The spring pieces can be made of elastic metal (such as spring steel) or polymers. The spring pieces on the end parts of the disc spring skeletons 8 are directly abutted against the distal disk 206, the proximal disk 205 or the connecting piece 203.

Figure 22:
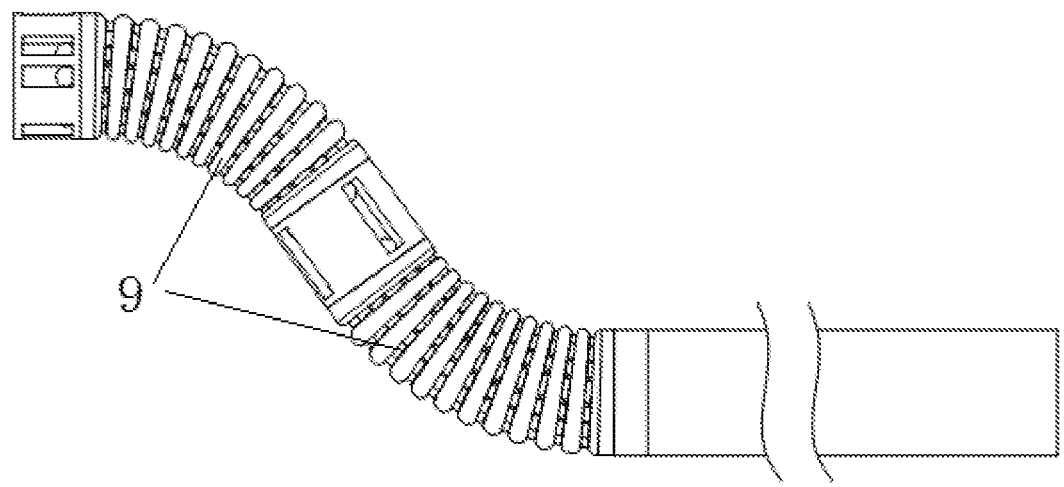
FIG. 22 is a schematic diagram when a deformable segment with combined motion of the present invention is provided with a bellows outer skeleton.
Figure 23:
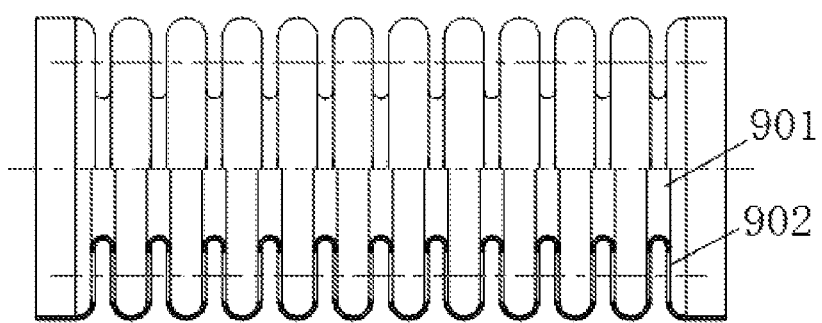
FIG. 23 is a schematic diagram of a bellows outer skeleton in FIG. 22.

As shown in FIGS. 22-23, bellows outer skeletons 9 can be sleeved outside the driving deformation part 209 and the linkage deformation part 210 of the deformable segment with combined motion 2 in the present invention. Each of the bellows outer skeletons 9 is provided with a skeleton passage 901 for the flexible center backbone 201 to pass through. Outer circumferential fins of the bellows skeletons 9 are provided with a plurality of through holes, and the through holes correspondingly presented in a straight line on the circumferential fins form a passage 902 for the tendons, the tightly wound springs or other elements to pass through. The bellows outer skeletons 9 can be made of elastic metal (such as spring steel) or polymers. The end parts of the bellows outer skeletons 9 are directly abutted against the distal disk 206, the proximal disk 205 or the connecting piece 203.

As shown in FIG. 21, the end-effector 4 comprises a rotating seat 404, a connecting disk 401, an opening and closing push-pull rod 405, an opening and closing driving tendon 402, a torque sheath pipe 403 and an execution instrument; the rotating seat 404 is rotatably arranged on the connecting disk 401; a movable opening and closing push-pull rod 405 is arranged in the rotating seat 404; the connecting disk 401 is connected with the flexible center backbone 201; a torque sheath pipe 403 is arranged in the flexible center backbone 201; the torque sheath pipe 403 is fixedly connected with the rotating seat 404; the opening and closing driving tendon 402 is arranged in the torque sheath pipe 403; the opening and closing driving tendon 402 is fixedly connected with the opening and closing push-pull rod 405; and the front end of the opening and closing push-pull rod 405 is connected with the execution instrument through a connecting rod assembly 406. In the present embodiment, the execution instrument is separating pliers. The opening and closing push-pull rod 405 is driven to move through the opening and closing driving tendon 402, so as to drive the separating pliers to open and close through the connecting rod assembly 406. The connecting rod assembly 406 is a four-connecting rod mechanism. The proximal end of the opening and closing driving tendon 402 extends out from the flexible center backbone 201 and then is connected with an electric push rod and driven by the electric push rod to move. The proximal end of the torque sheath pipe 403 extends out from the flexible central backbone 201 and then is connected with a motor through a transmission assembly and is driven by the motor to rotate. The transmission assembly can be an assembly of chain transmission, belt transmission or gear transmission. In addition, a chute is arranged in the rotating seat 404; a slide block 408 is arranged in the chute; a spring 407 is arranged between the slide block 408 and the bottom of the chute; the rear end of the opening and closing push-pull rod 405 is abutted against the slide block 408; and the opening and closing driving tendon 402 penetrates through the slide block 408 and the spring 407 and then is fixedly connected with the opening and closing push-pull rod 405.

As shown in FIG. 2, an outer cover 102 is arranged on the outer side of the proximal driving segment 1.

The present invention has the operating principle that:

When the present invention works, the present invention pulls the proximal driving tendon 101 to move to realize the deformation of the proximal driving segment 1, and pulls the distal driving tendon 302 to move to realize the deformation of the distal execution segment 3. The motion of the proximal driving tendon 101 can be transmitted to the connecting piece 203 in the middle of the deformable segment with combined motion 2 so as to deform the deformable segment with combined motion 2 to realize the expansion space required for surgeries such as single port laparoscopic surgery. Moreover, because the sum of lengths of the deformable segment with combined motion 2 remains unchanged during the linkage expansion deformation, the length of the distal driving tendon 302 in the deformable segment with combined motion 2 is not changed. Therefore, the deformation of the deformable segment with combined motion 2 does not affect the deformation of the distal execution segment 3. In addition, the lengths of the opening and closing driving tendon 402 and the torque sheath pipe 403 in the flexible center backbone 201 in the deformable segment with combined motion 2 are not changed. The deformation motion of the deformable segment with combined motion 2 does not affect the action of the end-effector 4.

The invention claimed is:

1. A deformable mechanism with combined motion, comprising:
    a proximal driving segment, a deformable segment with combined motion, a distal execution segment, and an end-effector,
    wherein the deformable segment with combined motion comprises a flexible center backbone, a plurality of tendons, a connecting piece, a proximal disk, and a distal disk,
    wherein a proximal end of the flexible center backbone and a proximal end of each of the plurality tendons are fixedly connected to the proximal disk, a distal end of each of the plurality of tendons is fixedly connected to the distal disk,
    wherein a distal end of the flexible center backbone extends through the distal disk into the distal execution segment and is connected with a connecting disk (401) at the end-effector,
    wherein the proximal driving segment is provided with a plurality of proximal driving tendons that extend through the proximal disk of the deformable segment with combined motion and are fixedly connected with the connecting piece,
    wherein the distal execution segment comprises a plurality of distal driving tendons each having a distal end fixedly connected to the connecting disk at the end-effector, and
    a proximal end extending through the deformable segment with combined motion and the proximal driving segment,
    wherein the end-effector comprises a rotating seat, a connecting disk, an opening and closing push-pull rod, an opening and closing driving tendon, and a torque sheath pipe, and
    wherein the rotating seat is rotatably arranged on the connecting disk, a movable opening and closing push-pull rod is arranged in the rotating seat, the connecting disk is connected with the flexible center backbone, a torque sheath pipe for driving rotation of the rotating seat is arranged in the flexible center backbone, and the opening and closing driving tendon for driving the opening and closing push-pull rod is arranged in the torque sheath pipe.

2. The deformable mechanism with combined motion according to claim 1, wherein the deformable segment with combined motion is provided with a deformation segment transition disk, the distal execution segment is provided with an execution segment transition disk, and the deformation segment transition disk and the execution segment transition disk are provided with a plurality of through holes.

3. The deformable mechanism with combined motion according to claim 1, wherein the deformable segment with combined motion is provided with a tightly wound spring, and the plurality of distal driving tendons extend along a spring.

4. The deformable mechanism with combined motion according to claim 1, wherein an inner passage is arranged in each of the plurality of tendons of deformable segment with combined motion, and the plurality of distal driving tendons extend along an inner passage in the corresponding the plurality of tendons of deformable segment with combined motion.

5. The deformable mechanism with combined motion according to claim 1, wherein the flexible center backbone is provided with spring layers of different rotating directions, and the flexible center backbone has a hollow interior.

6. The deformable mechanism with combined motion according to claim 1, wherein the deformable segment with combined motion and the proximal driving segment are connected through the connecting piece, and an outer skeleton is sleeved outside the proximal driving segment, the deformable segment with combined motion, and the distal execution segment.

7. The deformable mechanism with combined motion according to claim 6, wherein the outer skeleton is selected from the group consisting of transition disks, slot type outer skeleton, disk type outer skeleton, spring outer skeleton, disc spring skeleton, and bellows outer skeleton.

8. The deformable mechanism with combined motion according to claim 6, wherein a plurality of passages are arranged in the outer skeleton.

9. The deformable mechanism with combined motion according to claim 1, wherein a chute is arranged in the rotating seat, a slide block is arranged in the chute, a spring is arranged between the slide block and a bottom of the chute, a rear end of the opening and closing push-pull rod abuts the slide block, and the opening and closing driving tendon extends through the slide block and the spring and is fixedly connected with the opening and closing push-pull rod.

* * * * *